US006407133B2

(12) United States Patent
Hellstrand et al.

(10) Patent No.: US 6,407,133 B2
(45) Date of Patent: *Jun. 18, 2002

(54) TREATMENT AND PREVENTION OF REACTIVE OXYGEN METABOLITE-MEDIATED CELLULAR DAMAGE

(75) Inventors: Kristoffer Hellstrand, Gothenburg; Svante Hermodsson, Molndal, both of (SE); Kurt R. Gehlsen, Encinitas, CA (US)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/833,896

(22) Filed: Apr. 12, 2001

Related U.S. Application Data

(62) Division of application No. 09/227,455, filed on Jan. 8, 1999, now Pat. No. 6,242,473.

(51) Int. Cl.$^7$ ............................................. A61K 31/417
(52) U.S. Cl. ........................................................ 514/400
(58) Field of Search ........................................ 514/400

(56) References Cited

U.S. PATENT DOCUMENTS

| | | | |
|---|---|---|---|
| 4,573,996 A | 3/1986 | Kwiatek et al. | 604/897 |
| 4,597,961 A | 7/1986 | Etscorn | 424/28 |
| 4,839,174 A | 6/1989 | Baker et al. | 424/447 |
| 4,908,213 A | 3/1990 | Govil et al. | 424/447 |
| 4,943,435 A | 7/1990 | Baker et al. | 424/448 |
| 5,122,127 A | 6/1992 | Stanley | 604/890.1 |
| 5,284,647 A | 2/1994 | Niedballa et al. | 424/81 |
| 5,284,657 A | 2/1994 | Lu et al. | 424/435 |
| 5,288,497 A | 2/1994 | Stanley et al. | 424/440 |
| 5,328,454 A | 7/1994 | Sibalis | 604/20 |
| 5,336,168 A | 8/1994 | Sibalis | 604/20 |
| 5,424,198 A | 6/1995 | Levinson et al. | 435/69.2 |
| 5,474,527 A | 12/1995 | Bettinger | 604/19 |
| 5,612,029 A | 3/1997 | Bennett et al. | 424/94.64 |
| 5,662,920 A | 9/1997 | Santus | 424/435 |
| 5,676,969 A | 10/1997 | Wick et al. | 424/448 |
| 5,716,610 A | 2/1998 | Jack et al. | 424/78.05 |
| 5,770,425 A | 6/1998 | Anderson et al. | 435/226 |
| 5,804,203 A | 9/1998 | Hahn et al. | 424/401 |

FOREIGN PATENT DOCUMENTS

| | | |
|---|---|---|
| WO | 93/24144 | 12/1993 |
| WO | 95/03819 | 2/1995 |
| WO | 96/05289 | 2/1996 |

OTHER PUBLICATIONS

Larrea et al., Free Radical Biology and Medicine, 24/7–8 (1235–1241) 1998 (abstract).*
Mehta et al., Digestive Disease and Sciences 43/3 (646–651) 1998 (abstract).*
Rossi et al., Clinical Immunology and Immunopathology, 86/1(16–26) 1998 (abstract).*
Mizgerd et al., Current Microbiology, 31/2 (124–128) 1995 (abstract).*
Babior, et al., The Journal of Clinical Investigation, 52: 741–744 (Mar. 1973).
Bone, R.C. (1984) The adult respiratory distress syndrome: Treatment in the next decade. Respiratory Care. 29(3):249–262. XP–000882582.
Brune, et al. (1996) NK cell–mediated killing of AML blasts: role of histamine, monocytes and reactive oxygen metabolites. Eur. J. Haematol. 57:312–319.
Demling, R.H. (1988) The role of mediators in human ARDS. Journal of Critical Care. 3(1):66–72. XP–000882581.
Grisham et al. (1998) Modulation of leukocyte–endothelial interactions by reactive metabolites of oxygen and nitrogen: relevance to ischemic heart disease. Free Radical Biology & Medicine. 25:404–433.
Gross et al. (1994) Free radicals in inflammatory bowel diseases pathophysiology and therapeutic implications. Hepato–Gastroenterol. 41:320–327.
Imamura, et al., Pathology International, 47 : 16–24 (1997).
Kawas, et al. Patient Care, pp. 62–83, Nov. 15, 1996.
Paul et al., Biochim. Biophys. ACTA., 156 : 168–178 (1968).
Perez–Ruiz, et al., Journal of Virological Methods, 69 : 113–124 (1997).
Rovere et al. (1994) In vivo experimental demonstration that hyperhistaminism counteracts tumor growth. Oncology Reports. 1:175–177.
Simonyan, et al. (1988) Examination of gastric secretory function–involves using copper–zinc superoxidedismutase and histamine–di:hydrochloride as stimulator to increase information from method. Tern. Med. Inst. XP002135228 Abstract.
Thomas, et al., Neuroreport, 9(11): 2595–2600 (1998).
Van Der Poel, et al., The Lancet, 337 : 317–319 (Feb. 9, 1991).
Watanabe, et al. (1981) Stomach ulcer and lysosomal cathepsin. Tohoku Journal of Experimental Medicine. 134:39–44. XP000882611 Abstract.
Yonekura, et al. (1987) Influence of ascorbic acid supplementation on the toxic effects of dietary histamine in chicks. Japanese Poultry Science. 24:354–362. XP000885454 Abstract.

* cited by examiner

*Primary Examiner*—Phyllis G. Spivack
(74) *Attorney, Agent, or Firm*—Knobbe, Martens, Olson & Bear, LLP

(57) ABSTRACT

The present invention relates to a method for preventing and/or reducing cellular and tissue damage caused by reactive oxygen metabolites (ROMs) released by phagocytic or endothelial cells in response to various infectious disease states or pathologies. The methods of the present invention contemplate reducing ROM-mediated damage by reducing the production and release of ROMs.

7 Claims, No Drawings

TREATMENT AND PREVENTION OF REACTIVE OXYGEN METABOLITE-MEDIATED CELLULAR DAMAGE

This application is a division of Ser. No. 09/227,455 filed Jan. 8, 1999, U.S. Pat. No. 6,242,473.

BACKGROUND OF THE INVENTION

The present invention relates to methods for treating and/or preventing tissue and cell damage caused by reactive oxygen species in mammals. More specifically, the present invention relates to the prevention and/or reduction of tissue and cell damage through the administration of histamine and histamine agonists.

The complete reduction of one molecule of $O_2$ to water is a four-electron process. Oxidative metabolism continually generates partially reduced species of oxygen, which are far more reactive, and hence more toxic than $O_2$ itself. A one-electron reduction of $O_2$ yields superoxide ion ($O_2^-$); reduction by an additional electron yields hydrogen peroxide ($H_2O_2$), and reduction by a third electron yields a hydroxyl radical (OH.), and a hydroxide ion. Nitrous oxide (NO), is another interesting reactive oxygen metabolite, produced through an alternative pathway. Hydroxyl radicals in particular are extremely reactive and represent the most active mutagen derived from ionizing radiation. All of these species are generated and must be converted to less reactive species if the organism is to survive.

Particular cells of the immune system have harnessed the toxic effects of ROMs as an effector mechanism. Professional phagocytes, polymorphonuclear leukocytes (neutrophils, PMN), monocytes, macrophages, and eosinophils function to protect the host in which they reside from infection by seeking out and destroying invading microbes. These phagocytic cells possess a membrane-bound enzyme system which can be activated to produce toxic oxygen radicals in response to a wide variety of stimuli.

The "increased respiration of phagocytosis" (the respiratory burst) was reported and thought to be a result of increased mitochondrial activity providing additional energy for the processes of phagocytosis. It was later shown that a non-mitochondrial enzymatic system produced the increased levels of oxygen metabolites since the respiratory burst continued even in the presence of mitochondrial inhibitors such as cyanide and antimycin A. In 1968, Paul and Sbarra showed clearly that hydrogen peroxide was produced by stimulated phagocytes and in 1973 Babior and co-workers established that superoxide was a major product of the oxidase. (Paul and Sbarra, *Biochim Biophys Acta* 156(1):168–78 (1968); Babior, et al., *J Clin Invest* 52(3):741–4 (1973). It is now generally accepted that the enzyme is membrane bound, exhibits a preference for NADPH ($K_m=45$ μM) over NADH ($K_m=450$ μM), and converts oxygen to its one electron-reduced product, superoxide.

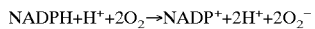

The hydrogen peroxide arises from subsequent dismutation of the superoxide.

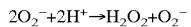

The enzyme activity is almost undetectable in resting (unstimulated) phagocytes, but increases dramatically upon stimulation. In patients with the rare genetic disorder chronic granulomatous disease (CGD), there is a severe predisposition to chronic recurrent infection. The neutrophils from these patients phagocytose normally but the respiratory burst is absent and NADPH oxidase activity (and radical production) is undetectable, indicating that the oxidase and its product, the reactive oxygen metabolites, have an important bactericidal function.

Neutrophils and macrophages produce oxidizing agents to break through the protective coats or other factors that protect phagocytosed bacteria. The large quantities of superoxide, hydrogen peroxide, and hydroxyl ions are all lethal to most bacteria, even when found in very small quantities.

While there are beneficial effects of these oxygen metabolites, it is clear that inappropriate production of oxygen metabolites can result in severely deleterious effects. Several disease states illustrate this point, including various inflammatory diseases, including rheumatoid arthritis, Crohn's disease, and Adult Respiratory Distress Syndrome (ARDS). An effective method to reduce and/or minimize the production and release of ROMs in patients suffering from a variety of disparate diseases would be a great boon to medicine and service to reduce and eliminate a substantial amount of human suffering.

SUMMARY OF THE INVENTION

The present invention provides a novel method for inhibiting and reducing enzymatically produced ROM-mediated oxidative damage. In accordance with one aspect of the present invention, there is provided a method for inhibiting and reducing enzymatically produced ROM-mediated oxidative damage in a subject comprising the step of administering a compound effective to inhibit the production or release of enzymatically produced reactive oxygen metabolites to a subject suffering from a condition caused or exacerbated by enzymatically produced ROM-mediated oxidative damage.

In one embodiment, the reactive oxygen metabolites are released constitutively. Alternatively, the reactive oxygen metabolites are released in response to a respiratory burst. In another embodiment of the present invention, the condition is selected from the group consisting of ARDS, ischemia or reperfusion injury, infectious disease, autoimmune or inflammatory diseases, and neurodegenerative diseases.

In another embodiment of the present invention, the compound is selected from the group consisting of histamine, $H_2$ receptor agonists, NADPH oxidase inhibitors, serotonin and serotonin agonists. One embodiment further comprising the step of administering an effective amount of a ROM scavenger. In the embodiment where a ROM scavenger is administered, the step of administering the ROM scavenger results in ROM scavenger catalyzed decomposition of ROMs. In still another embodiment, the scavenger is selected from the group consisting of catalase, glutathione peroxidase, ascorbate peroxidase, superoxide dismutase, glutathione peroxidase, ascorbate peroxidase, vitamin A, vitamin E, and vitamin C.

In accordance with still another aspect of the present invention, there is provided a method for treating a subject suffering from a disease state wherein phagocyte produced ROM-mediated oxidative damage can occur, comprising the steps of identifying a subject with a condition in which enzymatically generated ROMs released in response to a respiratory burst produce ROM-meditated oxidative damage and administering a compound effective to inhibit the production or release of ROMs.

In one embodiment, the condition is selected from the group consisting of ARDS, ischemia or reperfusion injury, infectious disease, autoimmune or inflammatory diseases, and neurodegenerative diseases. In another embodiment, the step of administering the compound further comprises administering a compound selected from the group comprising histamine, $H_2$ receptor agonists, serotonin, serotonin agonists, and NADPH oxidase inhibitors. Another embodiment, further comprising administering an effective amount of a ROM scavenger. In the embodiment where a ROM scavenger is administered, the step of administering the ROM scavenger results in the reactive oxygen metabolites scavenger catalyzed decomposition of reactive oxygen metabolites. In still another embodiment, the step of administering the reactive oxygen metabolites scavenger further comprises administering a compound selected from the group consisting of catalase, superoxide dismutase, glutathione peroxidase, and ascorbate peroxidase.

In accordance with still another aspect of the present invention, there is provided a pharmaceutical composition comprising a pharmaceutically acceptable carrier, a compound effective to inhibit the production or release of enzymatically generated ROMs and a compound effective to scavenge ROMs. In one embodiment, the compound effective to inhibit the production or release of ROMs is selected from the group consisting of histamine, $H_2$ receptor agonists, serotonin, serotonin agonists, and NADPH oxidase inhibitors. In another embodiment, the compound effective to scavenge ROMs is selected from the group consisting of catalase, glutathione peroxidase, ascorbate peroxidase, superoxide dismutase, glutathione peroxidase, ascorbate peroxidase, vitamin A, vitamin E, and vitamin C.

DETAILED DESCRIPTION OF THE PREFERRED EMBODIMENT

The present invention relates to compositions and methods for preventing and/or reducing cellular and tissue damage caused by reactive oxygen metabolites (ROMs) released by phagocytic or endothelial cells in response to various disease states or pathologies. The compositions and methods of the present invention are useful in preventing and treating a variety of disease states or pathological situations in which ROMs are produced and released. The compositions and methods of the present invention contemplate reducing ROM-mediated damage by reducing the production and release of ROMs.

A variety of reactive oxygen metabolites are produced in the monovalent pathway of oxygen reduction. These ROMs are enzymatically produced by phagocytes such as monocytes and polymorphonuclear neutrophils (PMNs) and frequently released in a respiratory burst. Neutrophils also produce ROMs constitutively. The constitutive production may contribute to ROM mediated cellular damage. Hydrogen peroxide and other ROMs play an important role in a host's immunological defenses. Nevertheless, ROMs produced in excessive amounts or at inappropriate times or locations, act to damage a host's cells and tissues, and thus can be detrimental to the host.

The effects of ROM production are many faceted. ROMs are known to cause apoptosis in NK cells. ROMs are also known to cause anergy and/or apoptosis in T-cells. The mechanisms by which ROMs cause these effects are not fully understood. Nevertheless, some commentators believe that ROMs cause cell death by disrupting cellular membranes and by changing the pH of cellular pathways critical for cell survival.

It is one of the surprising discoveries of the present invention that compounds that reduce the amount of ROMs produced or released by sources within a subject can facilitate the treatment and recovery of individuals suffering from a variety of medical conditions. The conditions contemplated as treatable under the present invention result from a disparate number of etiological causes. Nevertheless, they share a common feature in that their pathological conditions are either caused or exacerbated by enzymatically produced, ROM-mediated oxidative damage, caused by inappropriate and harmful concentrations of ROMs. Thus, the administration of compounds that inhibit the production or release of ROMs, or scavenge ROMs, alone or in combination with other beneficial compounds, provides an effective treatment for a variety of medical conditions.

The present invention contemplates compounds and methods that are efficacious in treating a variety of medical conditions wherein ROMs play an active, detrimental role in the pathological state of the disease. Such conditions include but are not limited to: Adult Respiratory Distress Syndrome (ARDS); ischemia/reperfusion injury such as stroke, myocardial infarction, complications of mechanical ventilation or septic shock; treatment of infectious diseases such as hepatitis C, acquired immunodeficiency syndrome (AIDS), or herpes virus infection; various autoimmune or inflammatory disorders where ROMs are believed to play a detrimental role such as multiple sclerosis (MS) and rheumatoid arthritis, and Inflammatory Bowel Diseases such as Crohn's disease and ulcerative colitis; various neurodegenerative disease where ROMs are thought to contribute to the disease state, such as ALS, Alzheimer's disease, and Parkinson's disease; as well as other clinical conditions wherein enzymatically produced ROMs can play an important role such as in radiation injury and cancer.

In a preferred embodiment, the present invention contemplates using various histamine and histamine-related compounds to achieve a beneficial reduction or inhibition of enzymatic ROM production and release or the net concentration thereof. The term "histamine" as used herein incorporates a variety of histamine and histamine related compounds. For example, histamine, the dihydrochloride salt form of histamine (histamine dihydrochloride), histamine diphosphate, other histamine salts, esters, or prodrugs, and $H_2$ receptor agonists are to be included. The administration of compounds that induce the release of endogenous histamine from a patient's own tissue stores is also included within the scope of the present invention. Such compounds include IL-3, retinoids, and allergens. Other ROM production and release inhibitory compounds such as NADPH oxidase inhibitors like diphenlyeneiodonium are also within the scope of the present invention. The use of serotonin and 5HT agonists in the present invention is also contemplated.

The compositions and methods of the present invention further contemplate administrating a variety of ROM scavengers in conjunction with the ROM production and release inhibiting compounds described above. Known scavengers of ROMs include the enzymes catalase, superoxide dismutase (SOD), glutathione peroxidase and ascorbate peroxidase. Additionally, vitamins A, E, and C are known to have scavenger activity. Minerals such as selenium and manganese can also be efficacious in combating ROM-mediated damage. It is intended that the present invention include the administration of the compounds listed and those compounds with similar ROM inhibitor activity.

The compositions and methods of the present invention also provide an effective means for preventing and/or inhibiting the release of enzymatically generated ROMs in excessive amounts or at inappropriate times or locations. One embodiment of the present invention also provides compounds and methods for the treatment of a variety of disease states that are complicated by the detrimental release of ROMs within a host or subject.

The administration of the compounds of the present invention can be alone, or in combination with other compounds effective at treating the various medical conditions contemplated by the present invention. For example, histamine can be used to treat a patient suffering from ARDS in conjunction with mechanical ventilation methods used to provide adequate oxygenation of the blood. Further, the compounds of the present invention can be used with a variety of anti-coagulation drugs administered by those of skill in the art, such as a tissue plasminogen activator (TPA), when treating a stroke or acute myocardial infarction. Also, the compounds of the present invention, such as histamine, can be administered with a variety of analgesics, anesthetics, or anxiolytics to increase patient comfort during treatment.

The use of the ROM inhibiting or scavenging compounds of the present invention can be by any of a number of methods well known to those of skill in the art. Such methods include parenteral delivery through subcutaneous, intravenous, intraperitoneal, or intramuscular injection. The compounds can be administered in an aqueous solution with or without a surfactant such as hydroxypropyl cellulose. Dispersions are also contemplated such as those utilizing glycerol, liquid polyethylene glycols, and oils. Antimicrobial compounds can also be added to the preparations. Injectable preparations can include sterile aqueous solutions or dispersions and powders that can be diluted or suspended in a sterile environment prior to use. Carriers such as solvents or dispersion media contain water, ethanol polyols, vegetable oils and the like can also be added to the compounds of the present invention. Coatings such as lecithins and surfactants can be used to maintain the proper fluidity of the composition. Isotonic agents such as sugars or sodium chloride can be added, as well as products intended to delay absorption of the active compounds such as aluminum monostearate and gelatin. Sterile injectable solutions are prepared according to methods well known to those of skill in the art and can be filtered prior to storage and/or use. Sterile powders can be vacuum or freeze dried from a solution or suspension. Sustained or controlled release preparations and formulations are also contemplated by the present invention and are discussed below. Any material used in the composition of the present invention should be pharmaceutically acceptable and substantially non-toxic in the amounts employed.

In another embodiment of the present invention, histamine administration occurs by administration through inhalation. In this administration route, histamine can be dissolved in water or some other pharmaceutically acceptable carrier liquid for inhalation, or provided as a dry powder, and then introduced into a gas or powder that is then inhaled by the patient in an appropriate volume so as to provide that patient with a measured amount of histamine.

Suitable infusion devices for use in the present invention include syringe pumps, auto injector systems and minipumps. Exemplary devices include the Ambulatory Infusion Pump Drive, Model 30, available from Microject Corp., Salt Lake City, Utah, and the Baxa Syringe Infuser, available from Baxa Corporation, Englewood, Colo. Any device capable of delivering histamine in the manner described below can be used with the present invention.

The infusion devices of the present invention preferably have an effective amount of histamine, histamine dihydrochloride, histamine phosphate, serotonin, a 5HT agonist, an $H_2$ receptor agonist or a substance which induces the release of an effective therapeutic amount of endogenous histamine contained therein. The device can be pre-loaded with the desired substance during manufacture, or the device can be filled with the substance just prior to use. Pre-filled infusion pumps and syringe pumps are well known to those of skill in the art. The active substance can be part of a formulation which includes a controlled release carrier, if desired. A controller is used with the device to control the rate of administration and the amount of substance to be administered. The controller can be integral with the device or it can be a separate entity. It can be pre-set during manufacture, or set by the user just prior to use. Such controllers and their use with infusion devices are well known to those of skill in the art.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released are also well known and can be used in the present invention.

In one embodiment, the compounds of the present invention are administered through a topical delivery system. The controlled release components described above can be used as the means to delivery the active ingredients of the present invention. A suitable topical delivery system comprises the active ingredients of the present invention in concentrations taught herein, a solvent, an emulsifier, a pharmaceutically acceptable carrier material, penetration enhancing compounds, and preservatives. Examples of topically applied compositions include U.S. Pat. Nos. 5,716,610 and 5,804,203, which are hereby incorporated by reference.

Controlled release preparations can be achieved by the use of polymers to complex or absorb the histamine. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

Hydrogels, wherein the histamine compound is dissolved in an aqueous constituent to gradually release over time, can be prepared by copolymerization of hydrophilic monoolefinic monomers such as ethylene glycol methacrylate. Matrix devices, wherein the histamine is dispersed in a matrix of carrier material, can be used. The carrier can be porous, non-porous, solid, semi-solid, permeable or impermeable. Alternatively, a device comprising a central reservoir of histamine surrounded by a rate controlling membrane can be used to control the release of histamine. Rate controlling membranes include ethylene-vinyl acetate copolymer or butylene terephthalate/polytetramethylene ether terephthalate. Use of silicon rubber depots are also contemplated.

Controlled release oral formulations are also well known. In one embodiment, the active compound is incorporated into a soluble or erodible matrix, such as a pill or a lozenge. Such formulations are well known in the art. An example of a lozenge used to administer pharmaceutically active compounds is U.S. Pat. No. 5,662,920, which is hereby incorporated by reference. In another example, the oral formulations can be a liquid used for sublingual administration. An example of pharmaceutical compositions for liquid sublingual administration of the compounds of the present invention are taught in U.S. Pat. No. 5,284,657, which is hereby incorporated by reference. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

For the purpose of parenteral administration, histamine or compounds which induce endogenous histamine release can be combined with distilled water, preferably buffered to an appropriate pH and having appropriate (e.g., isotonic) salt concentrations. Histamine formulations can be provided as a liquid or as a powder that is reconstituted before use. They can be provided as prepackaged vials, syringes, or injector systems.

Histamine can also be provided in septum-sealed vials in volumes ranging from about 0.5 to 100 ml for administration to an individual. In a preferred embodiment, the vials contain volumes of 0.5, 1, 3, 5, 6, 8, 10, 20, 50 and 100 ml. The vials are preferably sterile. The vials can optionally contain an isotonic carrier medium and/or a preservative. Any desired amount of histamine can be used to give a desired final histamine concentration. In a preferred embodiment, the histamine concentration is between about 0.01 mg/ml and 100 mg/ml. More preferably, the histamine concentration is between about 0.1 and 50 mg/ml. Most preferably, the histamine concentration is between about 1 mg/ml and 10 mg/ml. At the lower end of the volume range, it is preferred that individual doses are administered, while at the higher end it is preferred that multiple doses are administered.

In a preferred embodiment, transdermal patches, steady state reservoirs sandwiched between an impervious backing and a membrane face, and transdermal formulations, can also be used to deliver histamine and histamine agonists. Transdermal administration systems are well known in the art. Occlusive transdermal patches for the administration of an active agent to the skin or mucosa are scribed in U.S. Pat. Nos. 4,573,996, 4,597,961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference.

Present transdermal patch systems are designed to deliver smaller doses over longer periods of time, up to days and weeks, whereas the present invention would specifically deliver an effective dose of histamine in a range of between about 2 and 60 minutes, depending upon the dose, with a preferred dose being delivered within about 20–30 minutes. These patches allow rapid and controlled delivery of histamine. A rate-controlling outer microporous membrane, or micropockets of histamine dispersed throughout a silicone polymer matrix, can be used to control the release rate. Such rate-controlling means are described in U.S. Pat. No. 5,676,969, which is hereby incorporated by reference. In another preferred embodiment, the histamine is released from the patch into the skin of the patient in about 20–30 minutes or less. In a preferred embodiment, the histamine is released from the patch at a rate of between about 0.025 mg to 0.3 mg per minute for a dose of between about 0.2 mg and 5 mg per patch.

These transdermal patches and formulations can be used with or without use of a penetration enhancer such as dimethylsulfoxide (DMSO), combinations of sucrose fatty acid esters with a sulfoxide or phosphoric oxide, or eugenol. The use of electrolytic transdermal patches is also within the scope of the present invention. Electrolytic transdermal patches are described in U.S. Pat. Nos. 5,474,527, 5,336,168, and 5,328,454, the entire contents of which are hereby incorporated by reference.

In another embodiment transmucosal patches can be used to administer the active ingredients of the present invention. An example of such a patch is found in U.S. Pat. No. 5,122,127, which is hereby incorporated by reference. The described patch comprises a housing capable of enclosing a quantity of therapeutic agent where the housing is capable of adhering to mucosal tissues, for example, in the mouth. A drug surface area of the device is present for contacting the mucosal tissues of the host. The device is designed to deliver the drug in proportion to the size of the drug/mucosa interface. Accordingly, drug delivery rates can be adjusted by altering the size of the contact area.

The housing is preferably constructed of a material which is nontoxic, chemically stable, and non-reactive with the compounds of the present invention. Possible construction materials include: polyethylene, polyolefins, polyamides, polycarbonates, vinyl polymers, and other similar materials known in the art. The housing can contain means for maintaining the housing positioned against the mucosal membrane. The housing can contain a steady state reservoir positioned to be in fluid contact with mucosal tissue.

Steady state reservoirs for use with the compounds of the present invention will delivery a suitable dose of those compounds over a predetermined period of time. Compositions and methods of manufacturing compositions capable of absorption through the mucosal tissues are taught in U.S. Pat. No. 5,288,497, which is hereby incorporated by reference. One of skill in the art could readily include the compounds of the present invention in these and related compositions.

The steady state reservoirs for use with the present invention are composed of compounds known in the art to control the rate of drug release. In one embodiment, the transmucosal patch delivers a dose of histamine over a period of time from about 2 to 60 minutes. The steady state reservoir contained within the housing carries doses of histamine and other ROM production and release inhibitory compounds in doses from about 0.2 to 5 mg per patch. Transdermal patches that can be worn for several days and that release the compounds of the present invention over that period of time are also contemplated. The reservoirs can also contain permeation or penetration enhancers, as discussed above, to improve the permeability of the active ingredients of the present invention across the mucosal tissue.

Another method to control the release of histamine is to incorporate the histamine into particles of a polymeric material such as polyesters, polyamino acids, hydrogels, poly lactic acid, or ethylene vinylacetate copolymers.

Alternatively, instead of incorporating histamine into these polymeric particles, histamine is entrapped in microcapsules prepared, for example, by coacervation techniques, or by interfacial polymerization, for example hydroxymethylcellulose or gelatin-microcapsules, respectively, or in colloidal drug delivery systems, for example, liposomes, albumin microspheres, microemulsions, nanoparticles, and nanocapsules, or in macroemulsions. Such technology is well known to those of ordinary skill in pharmaceutical sciences.

Preferably, the histamine is injected, infused, or released into the patient at a rate of from about 0.025 to 0.2 mg/min. A rate of about 0.1 mg/min is preferred. The histmine is preferably administered over a period of time ranging from about 1, 3 or 5 minutes to about 30 minutes, with an upper limit of about 20 minutes being preferred, such that the total daily adult dose of histamine ranges from between about 0.4 to about 10.0 mg, with about 0.5 to about 2.0 mg being preferred. Histamine administered over longer periods of time, i.e., longer than about 30 minutes, has been found to result in decreased or lack of efficacy, while rapid administration over less than 1–3 minutes can cause more pronounced and serious side effects, which include anaphylaxis, heart failure, bronchospasm, pronounced flushing, discomfort, increased heart rate and respiratory rate, hypotension, and severe headache.

In another embodiment, histamine, a $H_2$-receptor agonist, at approximately 0.2 to 2.0 mg or 3–20 µg/kg, in a pharmaceutically acceptable form can be administered. ROM scavenging compounds can also be administered in combination with the ROM production and release inhibitory compounds described above.

The treatment can also include periodically boosting patient blood histamine levels by administering 0.2 to 2.0 mg or 3–20 µg/kg of histamine injected 1, 2, or more times per day over a period of one to two weeks at regular intervals, such as daily, bi-weekly, or weekly in order to establish blood histamine at a beneficial concentration such that ROM production and release is inhibited. The treatment is continued until the causes of the patient's underlying disease state is controlled or eliminated.

Administration of each dose of histamine can occur from once a day to up to about four times a day, with twice a day being preferred. Administration can be subcutaneous, intravenous, intramuscular, intraocular, oral, transdermal, intranasal, or rectal and can utilize direct hypodermic or other injection or infusion means, or can be mediated by a controlled release mechanism of the type disclosed above. Any controlled release vehicle or infusion device capable of administering a therapeutically effective amount of histamine over a period of time ranging from about 1 to about 30 minutes can be used. In a preferred embodiment, intranasal delivery is accomplished by using a solution of histamine in an atomizer or nebulizer to produce a fine mist which is introduced into the nostrils. For rectal delivery, histamine is formulated into a suppository using methods well known in the art.

Compounds that scavenge ROMs can be administered in an amount of from about 0.1 to about 10 mg/day; more preferably, the amount is from about 0.5 to about 8 mg/day; more preferably, the amount is from about 0.5 to about 8 mg/day; and even more preferably, the amount is from about 1 to about 5 mg/day. Nevertheless, in each case, the dose depends on the activity of the administered compound. The foregoing doses are appropriate for the enzymes listed above that include catalase, superoxide dismutase (SOD), glutathione peroxidase and ascorbate peroxidase. Appropriate doses for any particular host can be readily determined by empirical techniques well known to those of ordinary skill in the art.

Non-enzymatic ROM scavengers can be administered in amounts empirically determined by one of ordinary skill in the art. For example, vitamins A and E can be administered in doses from about 1 to 5000 IU per day. Vitamin C can be administered in doses from 1 µg to 10 gm per day. Minerals such as selenium and manganese can be administered in amounts from about 1 picogram to 1 milligram per day. These compounds can also be administered as a protective or preventive treatment for ROM mediated disease states.

In addition to histamine, histamine dihydrochloride, histamine phosphate, other histamine salts, esters, congeners, prodrugs, and $H_2$ receptor agonists, the use of serotonin, 5HT agonists, and compounds which induce release of histamine from the patient's own tissues is also included within the scope of the present invention. Retinoic acid, other retinoids such as 9-cis-retinoic acid and all-trans-retinoic acid, IL-3 and ingestible allergens are compounds that are known to induce the release of endogenous histamine. These compounds can be administered to the patient by oral, intravenous, intramuscular, subcutaneous, and other approved routes. The rate of administration should result in a release of endogenous histamine resulting in a blood plasma level of histamine of about 2 nmol/dl.

Administration of each dose of a compound which induces histamine release can occur from once per day to up to about four times a day, with twice per day being preferred. Administration can be subcutaneous, intravenous, intramuscular, intraocular, oral, or transdermal, and can incorporate a controlled release mechanism of the type disclosed above. Any controlled release vehicle capable of administering a therapeutically effective amount of a compound which induces histamine release over a period of time ranging from about one to about thirty minutes can be used.

The following predictive examples teach the methods of the present invention and the use of the disclosed ROM production and release inhibiting compounds. These examples are illustrative only and are not intended to limit the scope of the present invention. The treatment methods described below can be optimized using empirical techniques well known to those of ordinary skill in the art. Moreover, artisans of ordinary skill would be able to use the teachings described in the following examples to practice the full scope of the present invention.

EXAMPLES

Adult Respiratory Distress Syndrome

Adult Respiratory Distress Syndrome (ARDS) is a descriptive term that has been applied to many acute, diffuse infiltrative lung lesions of diverse etiologies when they are accompanied by severe arterial hypoxemia. The most common cause of ARDS is sepsis, however, diffuse pulmonary infections (e.g., viral, bacterial, fungal, or Pneumecyctosus); aspiration (e.g., gastric contents with Mendelson's syndrome, water from near drowning); inhalation of toxins and irritants (e.g., chlorine gas, $NO_2$, smoke, high concentrations of oxygen); narcotic overdose pulmonary edema; non-narcotic drug effects (e.g., nitrofurantoin); immunologic response to host antigens (e.g., Goodpasture's syndrome); and other conditions can lead to ARDS. Although different etiologies can lead to the pathological state known as ARDS, there are many common features present at the onset of respiratory failure.

The earliest sign of ARDS can come as an increase in respiratory frequency followed shortly by dyspnea. Arterial blood gas measurements in the earlier periods of treatment can disclose a depressed $P_{O_2}$ despite a decreased $P_{CO_2}$ so that alveolar-arterial difference for oxygen is increased.

At this stage administration of oxygen results in a significant increase in the arterial $P_{O_2}$. Physical examination can be unremarkable, although a few fine inspiratory rates can be audible. Radiographically, the lung fields can be clear or demonstrate only minimal and scattered interstitial infiltrates. With progression, the patient becomes cyanotic and increasingly dyspneic and tachypneic. Rales can become more prominent and easily heard throughout both the long fields along with regions of tubular breath sounds; the chest radiograph demonstrates diffuse, extensive bilateral interstitial and alveolar infiltrates.

Regardless of the initiating process, ARDS is invariably associated with increased liquid in the lungs. It is a form of pulmonary edema, although distinct from cardiogenic pulmonary edema because pulmonary capillary pressure is not elevated. Since hydrostatic pressures are not elevated, there is increased permeability of the alveolocapillary membranes that occurs via direct chemical injury. Inhaled toxic gases or elements associated with sepsis, bacterial endotoxins (gram-negative bacteria) or exotoxins (gram-positive bacteria) that stimulate monocytic phagocytes, resident macrophages, and polymorphonuclear leukocytes to adhere to endothelial surfaces and undergo a respiratory burst.

One ramification of the respiratory burst is the production of ROM mediated injury and the release of inflammation mediators such as leukotrienes, thromboxanes, and prostaglandins. The monocytic phagocytes, mainly macrophages in the alveoli and those lining the vasculature, also release oxidants, mediators, cytokines, and a series of degradative enzymes and peptides that directly damage endothelial and alveolar surfaces and cause polymorphonuclear leukocytes to release their lysosomal enzymes. Initially, the injury to the alveolocapillary membrane results in leakage of liquid, macromolecules, and cellular components from the blood vessels into the interstitial space and, with increasing severity, into the alveoli. Given the pathophysiology of ARDS, it should be noted that early administration of histamine can lessen the overall damage to the pulmonary system early-on in the process since such an administration reduces ROM production and release. Accordingly, reduction of ROM levels reduces ROM-mediated oxidative damage to cellular and tissue structures.

The treatment of an individual suffering from ARDS is discussed below, using the methods and compounds of the present invention.

Example 1

A patient is first identified having an injury to the lungs that would indicate the possible on-set of ARDS. At this point or prior, administration of the ROM production and release inhibitory compounds of the present invention, such as histamine, is initiated. Histamine, a $H_2$-receptor agonist, is administered through injection into the subject experiencing or about to experience ARDS at approximately 5 µg/kg. Additionally, the ROM scavenging compound catalase is also administered in combination with the histamine in an amount of 10 mg/day. The above procedure is repeated until an objective regression of symptoms is observed. In patients with complete responses, the frequency of therapy is reduced.

The reduction in the levels of ROM production and release is maintained by periodic histamine administrations. This entails administering 5–20 µg/kg of histamine injected 2 times per day, to inhibit ROM production and release. The treatment is continued until the pulmonary physiology stabilizes and/or the causative agents of the ARDS are removed.

Ischemia/Reperfusion Injury

Ischemia/reperfusion injury following stroke (blockage of a blood vessel, or rupture of a blood vessel in the brain) or acute myocardial infarction (heart stops, and blood cannot be pumped) has a common theme in that neutrophils when arrested in blood vessels become activated. This activation leads to the respiratory burst, or degranulation discussed above, resulting in the production and release of ROMs. These free radicals cause local tissue damage that can lead to vascular leakage and edema, thereby exacerbating the clinical situation of the stroke or infarction. In the lungs, this neutrophil/ROM damage is a major cause of acute respiratory distress syndrome (ARDS) following MI, mechanical ventilation and other states that can lead to low tissue blood flow/low oxygen tension situations. In the brain this can expand the area of tissue destruction, leading to irreversible brain damage. Thus, a compound that could prevent or reduce ROM-mediated damage caused by phagocytes could significantly protect normal tissue from destruction. The prevention and/or treatment of an individual suffering from ischemia or reperfusion injury are discussed below, using the methods and compounds of the present invention.

Stroke

Brain damage is often caused by the common abnormality called a "stroke."Strokes are often caused either by a ruptured blood vessel that allows hemorrhage into the brain or by the thrombosis of the major arteries supplying the brain. In either case, loss of the blood supply to brain tissue occurs. In addition to the loss of oxygen caused by an interruption of blood flow to the brain, phagocytes in the damaged area are often induced to produce a respiratory burst, causing the production and release of ROMs. The resulting increase in the concentration of ROMs augments brain tissue damage in addition to that caused by the lack of blood flow and oxygen.

Example 2

A patient presenting the symptoms of stroke is treated with histamine, which should be administered as soon as the diagnosis of stroke is made. Early administration prevents the occurrence of ROM mediated damage in individuals who have yet to experience a full blown stroke. Administration of the compounds can occur before, during and after the detection of stroke symptoms in the patient.

Histamine is injected subcutaneously in a sterile carrier solution into the patient experiencing or about to experience stroke at 15 µg/kg per day, in a pharmaceutically acceptable form. The above procedure is repeated daily for 5–7 days or until an objective regression of symptoms is observed.

Myocardial Infarction

Immediately after an acute coronary occlusion, blood flow ceases in the coronary vessels beyond the occlusion except from small amounts of collateral flow from surrounding vessels. The area of muscle that has either zero flow or reduced flow to the point where it cannot sustain cardiac function is said to be infarcted. Thus, this condition is known as myocardial infarction (MI).

Soon after the onset of the infarction, small amounts of collateral blood seeps into the infarcted area, and this, combined with progressive dilation of the local blood vessels, causes the area to become overfilled with stagnant blood. During this period of interrupted blood flow, professional phagocytes, polymorphonuclear leukocytes (neutrophils, PMN), monocytes, and macrophages become stimulated and produce a respiratory burst leading to cardiac muscle damage.

Death can result from the myocardial infarction if the extent of tissue damage is not limited. Restoration of cardiac output is also essential for the survival of the patient. Removal of the blockage that caused the myocardial infarction and restoration of blood flow to the cardiac muscle are also essential. In addition to standard MI treatment protocols well known in the medical arts, the administration of tissue plasminogen activator can also be used to treat myocardial infarction. For reference, see U.S. Pat. Nos. 5,770,425, 5,612,029, and 5,424,198, which are hereby incorporated by reference. Further, the ROM production and release inhibitory compounds of the present invention are administered to minimize tissue damage caused by ROM release as a result of the myocardial infarction.

Example 3

Histamine is administered to a patient presenting the symptoms of an MI. Histamine should be administered as soon as the diagnosis of MI is made. Administration to individuals who have yet to experience a full blown MI can also occur to prevent or reduce the magnitude of ROM-mediated damage if the MI comes to fruition. Administration is continued during and after the symptoms of myocardial infarction are detected.

Histamine, a $H_2$-receptor agonist, at approximately 10 $\mu$g/kg/day, in a pharmaceutically acceptable form is introduced by subcutaneous injection into a subject experiencing or about to experience MI. The above procedure is repeated daily for 7 days.

Subendocardial Myocardial Infarction

Myocardial infarction frequently occurs in the subendocardial muscle even when the epicardial portions of the heart muscle remain uninfarcted. This form of infarction occurs especially when the diastolic arterial pressure is very low or when the diastolic intraventricular pressure is very high. Most of the blood flow into the subendocardial arterial plexus occurs during diastole. Therefore, when the diastolic arterial pressure is very low—as occurs in patients who have aortic regurgitation, patent ductus arterious, or to a lesser extent arteriosclerosis—one can expect a high incidence of subendocardial myocardial infarction.

Example 4

Histamine is administered to a patient presenting subendocardial myocardial infarction, as described in Example 3. The administration of this compound results in the prevention of the release or production of ROMs that would have otherwise been released in response to the subendocardial myocardial infarction disease state.

Mechanical Ventilation

Endotracheal intubation and positive-pressure mechanical ventilation have direct and indirect effects on several organ systems, including the lung and upper airways, the cardiovascular system, and the gastrointestinal system. A variety of pulmonary complications attend mechanical ventilation, but oxygen toxicity is particularly relevant to the present invention. Oxygen toxicity is a potential complication when an $FiO_2$ of 0.6 or higher is required for more than 72 hours. The condition is thought to result from the generation of ROMs in the lung interstitium.

Example 5

Histamine is administered by intravenous injection to a patient undergoing mechanical ventilation. Histamine, a $H_2$-receptor agonist, is administered through daily injections to a patient receiving mechanical ventilation therapy at approximately 10 $\mu$g/kg/dose, in a pharmaceutically acceptable form. The administration is continued during the ventilation therapy or until the symptoms disappear. Diphenyleneiodonium, a NADPH oxidase inhibitor is also administered by intravenous injection.

The ROM inhibitory compound therapy is continued even after ventilation therapy has ceased, however, the frequency of ROM inhibitory compound therapy is reduced. The histamine is administered by subcutaneous injection 10 $\mu$g/kg/day for seven days.

Septic Shock

Circulatory shock, or the generalized inadequacy of blood flow throughout the body, to the extent that tissue damage occurs both because of a lack of oxygen and because of the generation of respiratory bursts, is often caused by physiological conditions where cardiac output is insufficient, as discussed above. Occasionally, a patient can have normal cardiac output, yet the person is in circulatory shock. This can result from excessive metabolism of the body so that even a normal cardiac output is inadequate, or from abnormal tissue perfusion patterns such that most of the cardiac output is passing through blood vessels that are not supplying the local tissues with nutrition. These conditions are seen most frequently in the type of shock called septic shock or blood poisoning.

Although there are many different varieties of septic shock because of the many different types of bacterial infection that can cause it, the different types share certain common features. Some features often seen in septic shock are: high fever; marked vasodilatation throughout the body, especially in the infected tissues; high cardiac output caused by the vasodilatation and by the effects of bacterial toxins on the body's metabolism; an increase in blood viscosity perhaps caused by red cell agglutination; and the development of microclots in widespread areas of the body, called disseminated intravascular coagulation.

In response to the bacterial infection and the increasing number of bacteria and bacterial toxins, the professional phagocytes undergo respiratory burst, and produce and release large quantities of ROMs and secondary cytokines such as tumor necrosis factor-alpha (TNF-α) and interleukin-1 (IL-1). An example of secondary cytokine mediated cell damage is found in the Shwartzman Reaction, where neutrophil mediated cell damage is thought to be activated by TNF and IL-1. Imamura S, et al., "Involvement of tumor necrosis factor-alpha, interleukin-1 beta, interleukin-8, and interleukin-1 receptor antagonist in acute lung injury caused by local Shwartzman reaction" Pathol Int. 47(1):16–24 (1997). This ROM and cytokine release augments the bacteria-mediated cell damage as these potent chemical compounds are disseminated throughout the body. Although released as a defensive measure by the cells of the immune system, the ROMs result in ROM-mediated cell damage and the secondary cytokines cause a rapid deterioration of the patient, resulting often in death.

Example 6

A patient presenting a systemic bacterial infection is selected for treatment with the compounds of the present invention. In the early stages of septic shock, the patient may not present signs of circulatory collapse. As the infection becomes more severe, however, the circulatory system can become involved in the bacterial infection.

Histamine administration occurs as soon as the diagnosis of septic shock is made. Administration of histamine to individuals who have yet to experience a full blown septic shock can also occur to prevent or reduce the magnitude of ROM-mediated damage and exacerbation of the shock state by the release of TNF-α or IL-1 if septic shock comes to fruition. Administration is continued during and after the symptoms of septic shock are detected.

Initially, histamine, at approximately 7 μg/kg, in a pharmaceutically acceptable form is injected subcutaneously in a sterile carrier solution into subjects experiencing or about to experience septic shock. The above procedure is repeated until an objective regression of symptoms is observed.

Treatment of Infectious Diseases

The production and release of ROMs is an active and important part of any immunological response to an invading pathogenic organism. The initial production and release of ROMs can serve to assist the body's immune system in destroying invading pathogens and to assist in the elimination of host cells that have been infected with an invading organism. Nevertheless, an excessive production of ROMs can pose a problem of its own to the host organism.

In certain chronic infectious diseases, the constitutive production and release of ROMs cause more harm to host cells than the benefits derived from the antibacterial or antiviral properties of ROM production. In those situations, patients who are combating pathogenic infections will benefit from the inhibition of ROM production and release. Accordingly, administration of the present invention's compounds are contemplated as efficacious for the treatment of various infectious diseases.

Hepatitis C

Hepatitis C (HCV) has become a significant health threat throughout the world. HCV is an RNA virus that specifically infects the liver. Chronic infection leads to liver malfunction, cirrhosis, and eventually death. Acute hepatitis C infections, however, are usually associated with subclinical disease, with only approximately one quarter of acute cases resulting in jaundice. When acute disease occurs, general symptoms of hepatitis are apparent, such as malaise, anorexia, nausea, and occasionally pain in the right upper abdomen. There are few other physical signs of disease, with hepatomegaly and splenomegaly occurring in only a small proportion of patients.

In an HCV infected patient, the main immune response comprises lymphocytic cells such as NK cells, followed by T-cells, and much of the damage to liver tissue is due both to the virus and to the patient's own inflammatory response in the liver by phagocytic cells. Liver damage caused by phagocytic cells results, in part, from ROM production. The presence of the ROMs can also block, inhibit or prevent lymphocytic cells from effectively dealing with the source of the infection. Thus, the ROM serve to harm the infected individual through two pathways. A compound like histamine, that blocks ROM production, would serve to eliminate or inhibit direct ROM mediated damage, and also function to facilitate and enhance NK cells and T-cells so that they respond better to the viral infection. The prevention and/or treatment of an individual suffering from an HCV infection are discussed below, using the methods and compounds of the present invention.

Although HCV infection can present a variety of clinical symptoms by which to identify the infection, an accurate diagnosis can only be achieved by assaying for specific markers of the virus. Initially, serodiagnosis can be accomplished by monitoring for the presence of circulating antibodies to HCV using commercially available immunoscreening kits. The time for seroconversion is variable and generally occurs within 7 to 31 weeks after infection from transfusion. A variety of additional tests can be performed on subjects presenting a positive ELISA reaction. One such test is the RIBA, which comprises the individual antigens separated on a paper strip (ven der Poel, C. L., et al., *Lancet* 337:317–319 (1991); hereby incorporated by reference). Another method used to determine viral load is via PCR. One such method utilizes reverse transcriptase PCR to amplify HCV RNA. (See, Perez-Ruiz M, et al., "Determination of HCV RNA concentration by direct quantitation of the products from a single RT-PCR," *J Virol Methods* 69:113–24 (1997); hereby incorporated by reference).

Currently, the only available treatment for chronic HCV infection is alpha-interferon (α-IFN) which has been shown to be minimally effective in patients with HCV. Unfortunately, α-IFN therapy requires continuous treatment, with approximately 70% of α-IFN responding patients relapsing to a more progressive disease state. Moreover, there are a number of side effects of interferon therapy known, such as 60% to 80% of patients experiencing flu-like symptoms, increasing levels of irritability, fatigue, depression, anorexia, nausea, rashes, alopecia, thrombocytopenia, and leukopenia.

The compounds of the present invention are administered through the routes of administration discussed above in the doses described above, either alone or in conjunction with an HCV antiviral compound. The administration of these compounds results in the prevention of release or production of ROMs that would have otherwise been released in response to the HCV infection. The compounds of the present invention are administered to a patient presenting the symptoms of HCV infection. The ROM production and release inhibiting compounds of the present invention should be administered as soon as appropriate following the diagnosis of HCV infection.

Example 7

An individual suffering from an HCV infection is identified. Upon diagnosis of an HCV infection, a treatment course should commence. In addition to the administration of an active anti-HCV compound, the administration of the compounds of the present invention is efficacious in treating HCV infected individuals. For example, histamine, at approximately 12 μg/kg/day in a pharmaceutically acceptable form is administered through a controlled release vehicle, such as a suppository, into a subject experiencing an HCV infection.

The above procedure is continued for twelve to eighteen months to resolve the viral infection. The ROM scavenging compound vitamin E is also administered in combination with the histamine injection, in an amount of 5 mg/day. The treatment is continued until the patient's underlying viral infection is controlled or eliminated.

Autoimmune/Inflammatory Disorders

The etiology of several autoimmune disorders share the common feature of an over-reactive inflammatory response as a contributing factor to the pathology of the disease. A common denominator of this shared feature is the release of ROMs by phagocytic cells at the site of tissue injury. The neurodegenerative disease multiple sclerosis (MS) illustrates this situation. In MS, autoreactive T-cells begin to attack the myelin basic protein found in the protective myelin sheath of neurons. The initial insult is followed by worsening of the pathology caused by phagocytes and an over-reactive inflammatory response leading to further neuronal damage caused by the release of ROMs. Thus, the presence of ROMs accelerates neuronal damage and contributes to nervous system damage. A compound such as histamine could significantly reduce the ROM-mediated damage and allow for other treatments using cytokines such as gamma or beta interferons, and eliminate or change the need for steroidal treatments that can have other problematic effects. Histamine is used alone or in combination in this situation.

Multiple Sclerosis (MS)

The compounds of the present invention are administered to a patient presenting the symptoms of MS. They can be administered alone or in conjunction with other compounds efficacious in treating or controlling the MS disease state. The administration of these compounds results in the prevention of release or production of ROMs that would have otherwise been released in response to the MS disease state. The ROM production and release inhibiting compounds of the present invention should be administered as soon as the diagnosis of MS is made. Administration is continued during and after the hallmarks of the MS disease state are detected.

Example 8

Histamine, a $H_2$-receptor agonist, is administered to a patient diagnosed as suffering from MS in a dose of 7 :g/kg in a pharmaceutically acceptable form. Initially, the histamine is injected intramuscularly in a sterile carrier solution. The ROM scavenging compound superoxide dismutase is also administered at 7 mg/day. Subsequent treatments are administered through an implanted infusion device that provides a dose of histamine at 15 $\mu$g/kg/day. Implantation of the infusion device is performed using standard techniques well known in the art.

The above-described treatment is continued until an objective regression of symptoms is observed. New infusion devices are implanted to replace those that expend their histamine supply. In the event the subject presents an increase in neurodegeneration, periodic boosting of the histamine levels is achieved by administering additional histamine doses in 2 $\mu$g/kg doses by inhalation over a period of 5 times per day to control ROM production and release and to prevent additional ROM mediated neurodegenerative damage. The treatment is continued for the life of the patient.

Rheumatoid Arthritis

Rheumatoid arthritis is another autoimmune pathology that begins with local tissue damage in the joints that leads to further tissue damage mediated by autoreactive T-cells and followed by infiltration of pro-inflammatory cells like phagocytes which increase the damage by releasing ROMs. Much of the ROM free radical damage could be prevented by treating with a compound like histamine to block phagocyte derived ROMs.

The compounds of the present invention are administered through the routes of administration discussed above in the doses described above, either alone or in conjunction with other compounds efficacious in treating or controlling rheumatoid arthritis. The administration of these compounds results in the prevention of release or production of ROMs that would have otherwise been released in response to the rheumatoid arthritis disease state. The compounds of the present invention are administered to a patient presenting the symptoms of rheumatoid arthritis. The ROM production and release inhibiting compounds of the present invention should be administered as soon as the diagnosis of rheumatoid arthritis is made. Administration is continued during and after the hallmarks of the rheumatoid arthritis disease state are detected.

Example 9

Histamine, a $H_2$-receptor agonist, is administered to a patient diagnosed with arthritis in a dose approximately 8 $\mu$g/kg, in a pharmaceutically acceptable form. The histamine is initially injected intravenously in a sterile carrier solution into a subject suffering from rheumatoid arthritis. Thereafter, the histamine is administered transdermally in the form of a cream to those sites of the subject's body experiencing arthritis.

Application of the cream is repeated until a sustained objective regression of symptoms is observed. The therapy is continued even after a partial response is observed. In patients with complete responses, the frequency of therapy can be reduced to weekly administrations.

The treatment also includes periodically boosting patient blood histamine levels by administering a 8 $\mu$g/kg dose of histamine injected intramuscularly, at regular weekly intervals. The treatment is continued until the causes of the patient's underlying rheumatoid arthritis disease state are controlled or eliminated.

Inflammatory Bowel Disease

Inflammatory bowel disease (IBD) is a general term for a group of chronic inflammatory disorders of unknown cause involving the gastrointestinal (GI) tract. Crohn's disease and ulcerative colitis are both chronic inflammatory disorders that fall within the rubric of IBD. Both diseases have pronounced inflammation in the small intestinal mucosal tissue that can extend to other layers of the organ. Phagocytic cells are the primary drivers of the inflammatory reaction. As these cells release ROMs in response to the inflammation, the intestinal mucosa is damaged, leading to potentially serious consequences for the patient, including sepsis. A compound that prevents the production and release of ROMs could significantly impact on the pathogenesis of these diseases.

The compounds of the present invention are administered through the routes of administration discussed above in the doses described above, either alone or in conjunction with other compounds efficacious in treating or controlling IBD. The compounds of the present invention are administered to a patient presenting the symptoms IBD. The ROM production and release inhibiting compounds of the present invention should be administered as soon as the diagnosis of IBD is made. Administration is continued during and after the hallmarks of the IBD state are detected.

Example 10

Histamine, a $H_2$-receptor agonist, is administered to a patient presenting the symptoms of IBD. Histamine is administered rectally at approximately 20 :g/kg/dose in a pharmaceutically acceptable form, in the form of a suppository.

The above procedure is repeated daily until an objective regression of symptoms is observed. The therapy is continued even after a partial response is observed. In patients with complete responses, the frequency of therapy can be reduced to weekly administrations.

The treatment can also include periodically boosting patient blood histamine levels by administering 10 μg/kg/day of histamine injected subcutaneously at regular bi-weekly intervals. The treatment is continued until the causes of the patient's underlying IBD state are controlled or eliminated.

Neurodegenerative Diseases

ROM mediated cellular damage can be relevant to a number of neurodegenerative diseases such as ALS, Parkinson's disease, and Alzheimer's. The production and release of ROMs can cause or exacerbate the neurodegeneration of these diseases. Accordingly, the administration of the ROM production and release inhibiting compounds of the present invention are contemplated as being safe and effective for the treatment of a wide range of neurological disorders in which ROM mediated cellular damage plays a clinical role.

Amyotrophic Lateral Sclerosis (Lou Gehrig's Disease)

Amyotrophic lateral sclerosis (ALS) is also called Lou Gehrig's disease. It is a fatal disorder characterized by progressive degeneration of the motor cells in the spinal cord and brain (central nervous system), which inhibits nerve impulses from being sent to the muscles. Eventually, a person who has ALS experiences muscle weakness and wasting, particularly of the muscles used to move the arms and legs and muscles involved in speech, swallowing, and breathing. The cause is unknown and there currently is no cure for ALS.

It appears that ALS can be caused by complex inheritance, including both genetic and environmental factors. So far, one gene has been identified which is involved in the development of ALS in some families showing autosomal dominant inheritance. The gene is called superoxide dismutase 1 (SOD1), which is located on chromosome 21q22.

SOD1 is a member of a family of metalloenzymes characterized by an ability to dismutate $O_2^-$, i.e., to catalyze the conversion of $O_2^-$; the product of spontaneous and enzyme-catalyzed oxidation, into $H_2O_2$ and $O_2$. Behaving as a reductant or oxidant, $O_2^-$ gives rise to reactive molecules that can injure cells by a variety of mechanisms.

In view of this genetic link between ALS and the ROM pathway, the present invention contemplates utility in treating ALS. The symptoms of ALS include: tripping and falling, loss of motor control in hands and arms, difficulty speaking, swallowing and/or breathing, persistent fatigue, and twitching and cramping, sometimes quite severely. ALS strikes in mid-life. These symptoms are caused by the loss of motor neurons resulting in muscle weakness and wasting, and paralysis.

Example 11

A patient presenting symptoms of ALS is treated by administering the compounds of the present invention as soon as the diagnosis of ALS is made. The treatment is initiated by administering histamine using a sublingual composition at 5 μg/kg/day, in a pharmaceutically acceptable form, that is ingested orally by the subject suffering from ALS. The histamine is administered in conjunction with other compounds efficacious in treating or controlling ALS.

Following the injection, the patient is administered histamine at 5 mg/day in conjunction with vitamin A at 3000 IU/day, vitamin C at 1000 mg/day, vitamin E at 600 IU/day, selenium at 50 μg/day and manganese at 25 μg/day. These components can be formulated into a tablet for ease of administration.

The above procedure is repeated until an objective regression of symptoms is observed. The therapy can be continued even after a partial response is observed. In the event symptoms of ALS increase, the patient is to receive periodic boostings of histamine levels by the administration of 5 μg/kg/day of histamine by nasal administration at regular two week intervals. The treatment is continued until the causes of the patient's underlying ALS state are controlled or eliminated, or for the life of the patient.

Alzheimer's Disease

In Alzheimer's disease, the usually highly ordered nerve cells of the brain become extremely disorganized, and form neurofibrillary tangles. Dementia develops as the extent of neurofibrillary tangles increase. The cause of Alzheimer's disease is unknown. Senile plaques, accumulations of cellular debris surrounding a central core of beta-amyloid peptide, can play a role. Beta-amyloid peptide was first identified in the 1980's, some 70 years after Alzheimer identified senile plaques. For reasons that remain unclear, beta-amyloid accumulates in the brain tissue of people with Alzheimer's and presumably plays a role in destroying it.

Alzheimer disease (AD) is a clinical-neuropathological diagnosis. Affected individuals have slowly progressive dementia, gross cerebral cortical atrophy by neuroimaging studies and microscopic A Beta amyloid neuritic plaques, intraneuronal neurofibrillary tangles, and amyloid angiopathy at postmortem examination. The numbers of plaques and tangles must exceed those found in non-demented age-matched controls, and guidelines exist for these quantitative changes. The plaques should stain positively with A Beta amyloid antibodies and negative for prion antibodies.

The clinical diagnosis of AD (prior to autopsy confirmation) is correct about 80–90% of the time. AD typically begins with subtle and poorly recognized failure of memory. Slowly, over a period of years, the memory loss becomes more severe and eventually incapacitating. Other common symptoms include confusion, poor judgment, language disturbance, agitation, withdrawal, and hallucinations. Some patients can develop seizures, Parkinsonian features, increased muscle tone, myoclonus, incontinence, and mutism. Death usually results from general inanition, malnutrition, and pneumonia. The typical clinical duration of the disease is 8–10 years with a wide-range of 1–25 years.

It has been reported that the ingestion of anti-oxidants, compounds that promote the metabolism of ROMs to less reactive forms once they are synthesized and released, have had a positive effect of Alzheimer's patients. For example, Czech researchers gave the antioxidant drug selegiline to 173 people with mild to moderate Alzheimer's disease. After six months, their memory improved significantly. In another study, selegiline enhanced the benefits of tacrine (Cognex), one of the two drugs currently approved for Alzheimer's treatment. (Kawas, C. et al. "Treating Alzheimer's Disease: Today and Tomorrow," *Patient Care* (Nov. 15, 1996) pp. 62–83). It should be noted, however, that this report only addresses ROMs after they are synthesized and released. In view of the correlation between anti-oxidants and the Alzheimer's disease state, the compounds of the present invention are contemplated as having utility in the treatment of Alzheimer's disease by preventing or inhibiting the formation and release of ROMs.

Example 12

A patient presenting symptoms of AD is treated by administering the compounds of the present invention as soon as the diagnosis of AD is made. Histamine, a $H_2$-receptor agonist, at a 5 μg/kg/dose, in a pharmaceutically acceptable form is injected subcutaneously in a sterile carrier solution into the subject. The histamine is administered in conjunction with other compounds efficacious in treating or controlling AD and known to those of ordinary skill in the art.

The above procedure is repeated until an objective regression of symptoms is observed. The treatment also include periodically boosting patient blood histamine levels by administering 5 μg/kg/day of histamine at regular weekly intervals. The treatment is continued until the neurodegeneration responsible for the pathological condition of AD is controlled or eliminated, or for the life of the patient.

Parkinson's Disease

Parkinson's disease (PD), which is also known as paralysis agitans, results almost invariably from widespread destruction of the substantia nigra but is often associated also with lesions of the globus pallidus and other related areas. It is characterized by (1) rigidity of the musculature either in widespread areas of the body or in isolated areas, (2) tremor at rest of the involved areas in most but not all instances, and (3) a serious inability to initiate movement, called akinesia.

Certain commentators have seen oxidative stress as a possible cause of PD. Oxidative stress can play an important role in the creation of the Parkinson's disease state. Recently, the monoamine oxidase-B inhibitor L-deprenyl (Selegiline), a drug effective in the treatment of PD and possibly Alzheimer's disease, was shown to induced rapid increases in NO production in brain tissue and cerebral vessels. Vasodilatation was produced by endothelial NO-dependent as well as NO-independent mechanisms in cerebral vessels. The drug also protected the vascular endothelium from the toxic effects of amyloid-beta peptide. These novel actions of selegiline can protect neurons from ischemic or oxidative damage and suggest new therapeutic applications for L-deprenyl in vascular and neurodegenerative diseases. Thomas et al, Neuroreport, 9(11):2595–600 (1998). The efficacy of this compound supports the role oxidative stress in the Parkinson's disease state.

In view of these observations, the compounds of the present invention are contemplated as an effective treatment of PD, either when used alone or when the compounds of the present invention are used combination with other PD treatments.

Example 13

A patient presenting symptoms of PD is treated by administering the compounds of the present invention as soon as the diagnosis of PD is made. Histamine, a $H_2$-receptor agonist, at 5 μg/kg/day, in a pharmaceutically acceptable form is given by a transmucosal patch to subjects suffering from PD. The histamine is administered in conjunction with other compounds efficacious in treating or controlling PD that are well known in the art.

The therapy can be continued even after a partial response has been observed. In patients with complete responses, the frequency of therapy is reduced to weekly applications of histamine with transmucosal patches when an objective regression of symptoms is observed.

Other Disease States

Radiation Injury

Ionizing radiation is a harmful form of energy that damages tissue through the action of charged particles. Damage can result to tissues exposed to ionizing radiation through the effect of the energy on water, oxygen, and other molecules with the formation of ROMs, such as free hydroxyl radicals and other highly reactive oxygen species. Moreover, tissue damage and destabilization of homeostatic equilibrium due to overexposure to radiation can result in a systemic respiratory burst from professional phagocytes. This burst results in a release of ROMs causing tissue damage.

Example 14

A patient exposed to toxic levels of ionizing radiation is treated by administering the compounds of the present invention at the time of treatment with an appropriate therapy or a diagnosis of radiation toxicity. Histamine, a $H_2$-receptor agonist, at 17 μg/kg, is injected subcutaneously in a pharmaceutically acceptable form into subjects suffering from radiation toxicity. The histamine is administered in conjunction with other compounds efficacious in treating or controlling radiation poisoning that are well known to those of skill in the art.

The above procedure is repeated until an objective regression of symptoms is observed. The therapy is continued even after a partial response has been observed. In patients with complete responses, the frequency of therapy is reduced.

The treatment can also include periodically boosting patient blood histamine levels by administering 5 μg/kg of histamine injected once per day over a period of one to two weeks at regular intervals, such as daily, so that ROM production and release is inhibited.

Conclusion

We have discovered that the administration of compounds that inhibit the production and release of ROMs is instrumental in treating and preventing ROM mediated cell and tissue damage. The detrimental effects of unwanted ROMs are removed when the compounds of the present invention are administered in accordance with the methods taught herein. Further, the administration of ROM scavengers can assist in reducing the negative effects of unwanted ROM production.

Finally, the forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the present invention.

What is claimed is:

1. A method for treating a subject suffering from an infectious disease comprising:
   identifying a subject presenting the symptoms of the infectious disease caused or exacerbated by the release of ROMs from phagocytic cells resulting in ROM-mediated oxidative damage; and
   administering a compound effective to inhibit the production or release of the ROMs, wherein the compound is histamine.

2. The method of claim 1, wherein the infectious disease is selected from the group consisting of a virus, a bacteria, and fungus.

3. The method of claim 2, wherein the virus is Hepatitis C, human immunodeficiency virus, or a herpes virus.

4. The method of claim 1, wherein the infectious disease is sepsis.

5. The method of claim 1, further comprising the step of administering an effective amount of a ROM scavenger.

6. The method of claim 5, wherein the ROM scavenger is selected from the group consisting of catalase, glutathione peroxidase, ascorbate peroxidase, superoxide dismutase, glutathione peroxidase, ascorbate peroxidase, vitamin A, vitamin E, and vitamin C.

7. The method of claim 5, wherein administration of the ROM scavenger is accomplished by a method selected from the group consisting of injection, intramuscular injection, subcutaneous injection, implanted infusion device, inhalation, transdermal diffusion, and suppository.

* * * * *